United States Patent [19]

Davidson

[11] Patent Number: 4,818,110

[45] Date of Patent: Apr. 4, 1989

[54] METHOD AND APPARATUS OF USING A TWO BEAM INTERFERENCE MICROSCOPE FOR INSPECTION OF INTEGRATED CIRCUITS AND THE LIKE

[75] Inventor: Mark Davidson, Palo Alto, Calif.

[73] Assignee: KLA Instruments Corporation, Santa Clara, Calif.

[21] Appl. No.: 860,308

[22] Filed: May 6, 1986

[51] Int. Cl.$^4$ .............................................. G01B 9/02
[52] U.S. Cl. ..................................... 356/358; 356/359
[58] Field of Search ............... 356/358, 359, 384, 387, 356/372, 376

[56] References Cited

U.S. PATENT DOCUMENTS

| 4,072,422 | 2/1978 | Tanaka | 356/351 |
| 4,340,306 | 7/1982 | Balasubramanian | 356/360 |
| 4,641,971 | 2/1987 | Korth | 356/357 |

OTHER PUBLICATIONS

Applied Optics, 11/1967, vol. 6, No. 11, "The Determination of the Absolute Contours of Optical Flats", by Primak, pp. 1917–1923.
Diamond, "Interference Microscope for Testing Surfaces", *Industrial Diamond Review*, vol.–6, pp. 276–279, 9/46.
Forman, "The Zygointerferometer System", *Proc. SPIE*, vol. 192, pp. 41–48, 1979.

*Primary Examiner*—David C. Nelms
*Assistant Examiner*—Matthew W. Koren
*Attorney, Agent, or Firm*—Rosenblum, Parish & Bacigalupi

[57] ABSTRACT

A specially adapted Linnik microscope is used in combination with a video camera, a wafer transport stage and data processing electronics to form a novel inspection apparatus based on the use of the two beam interference microscope. The apparatus can utilize either broad band or narrow band light to develop a plurality of interference images taken at different axial positions relative to the surface under investigation. The point-by-point brightness along scan lines across such images is then used to develop data which is proportional to the degree of coherence (or to the fringe amplitude, the variance of the fringes, or the amplitude of oscillation of the fringes) as the optical path difference is varied in a two beam optical or acoustic microscope.

16 Claims, 6 Drawing Sheets

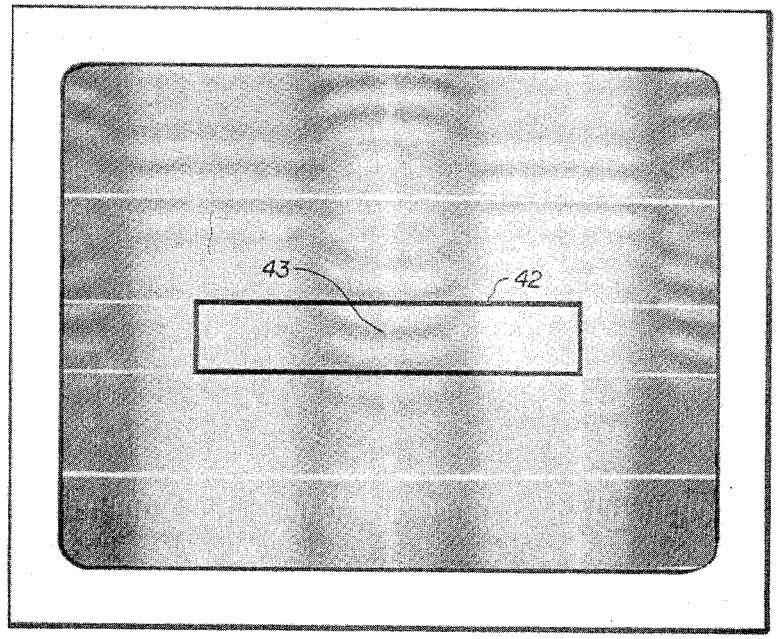
FIG_ 4
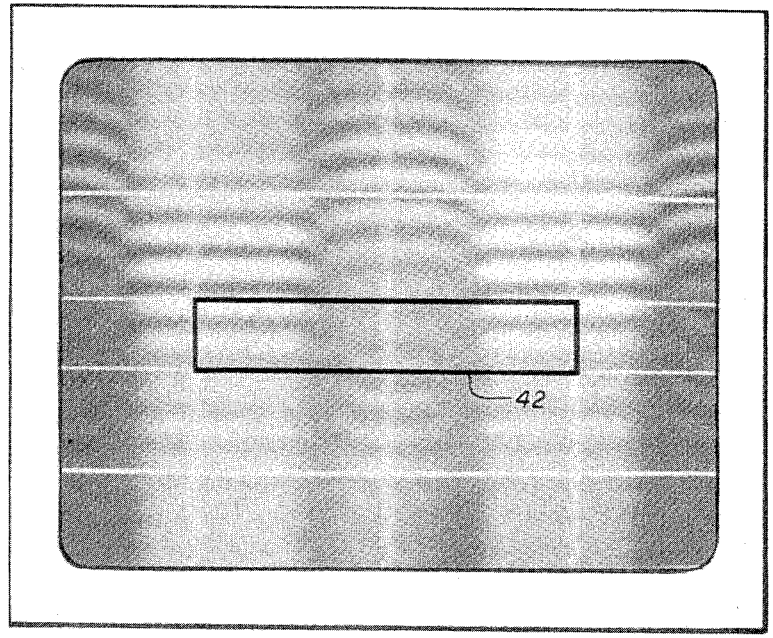
FIG_ 5

METHOD AND APPARATUS OF USING A TWO BEAM INTERFERENCE MICROSCOPE FOR INSPECTION OF INTEGRATED CIRCUITS AND THE LIKE

BACKGROUND OF THE INVENTION

1. Field of the Invention

The present invention relates generally to precision optical inspection methods and apparatus, and more particularly to a method and apparatus for performing microscopic inspection and measurement of integrated circuit wafer geometry using interference microscopy in combination with electronic image processing.

2. Discussion of the Prior Art

It has long been desired that means be provided to inspect and measure the characteristics of microminiature surfaces such as those formed in integrated circuit wafers. One such characteristic of interest is the line widths of the various traces produced on a wafer surface during IC device manufacture.

One prior art technique for integrated circuit metrology includes the use of an ordinary microscope with some form of electronic detector positioned at the image plane. For example, video cameras, scanning slits (see U.S. Pat. No. 4,373,817), shearing systems and linear arrays, have all been used as detectors with ordinary microscopes. However, the capability of the ordinary microscope is limited in that it can only measure the intensity of the optical wave amplitude and cannot measure the complex phase of the amplitude. As a consequence, the three-dimensional nature of integrated circuit surfaces makes use of the classical microscope impractical for precision surface inspections and measurements of this type.

Other prior art techniques have used confocal laser scanning microscopes to obtain three dimensional data relating to integrated circuit surfaces. A rather thorough treatment of the subject may be found in T. Wilson and C. Shepard (1984), *Theory and Practice of Scanning Optical Microscopy*, Academic Press.

Aside from the complexity and relatively high cost associated with the use of confocal laser devices and techniques, the fact that such techniques use monochromatic light makes them subject to inaccuracies caused by destructive interference for certain thicknesses of transparent films often found in semiconductor devices.

SUMMARY OF THE PRESENT INVENTION

It is therefore a principal object of the present invention to provide an improved method and apparatus for accomplishing three dimensional inspection of integrated circuits and the like.

Another object of the present invention is to provide an improved synthetic imaging technique utilizing a two beam interference microscope.

Still another object of the present invention is to provide a method and apparatus by which the top width, bottom width and height of an integrated circuit line may be accurately measured.

Briefly, a preferred embodiment of the present invention includes a specially adapted Linnik microscope in combination with a video camera, a wafer transport stage and data processing electronics to form a novel inspection apparatus based on the use of the two beam interference microscope. The apparatus can utilize either broad band or narrow band light to develop a plurality of interference images taken at different axial positions relative to the surface under investigation. The point-by-point brightness along scan lines across such images is then used to develop data which is proportional to the degree of coherence (or to the fringe amplitude, the variance of the fringes, or the amplitude of oscillation of the fringes) as the optical path difference is varied in a two beam optical or acoustic microscope.

Among the advantages of the present invention are that it provides a much simpler and more economical technique than those using the confocal microscope.

Another advantage is that it can use white light rather than monochromatic light and as a result, can have a signal-to-noise ratio which is not degraded by coherent speckle effects which affect any coherent optical system. Moreover, by using white light the possibility of destructive interference for certain thicknesses of transparent films is eliminated.

Furthermore, the theoretical resolution along the optical axis appears to be better than that for a confocal microscope because the short coherence length of white light effectively reduces the depth of focus of the instrument. Empirically, it also appears that the present invention substantially improves the lateral resolution of the microscope, at least for the purpose of measuring linewidths of integrated circuits.

These and other objects and advantages of the present invention will no doubt become apparent to those skilled in the art after having read the following detailed description of the preferred embodiments which are illustrated in the several figures of the drawing.

IN THE DRAWING

Figure 2:
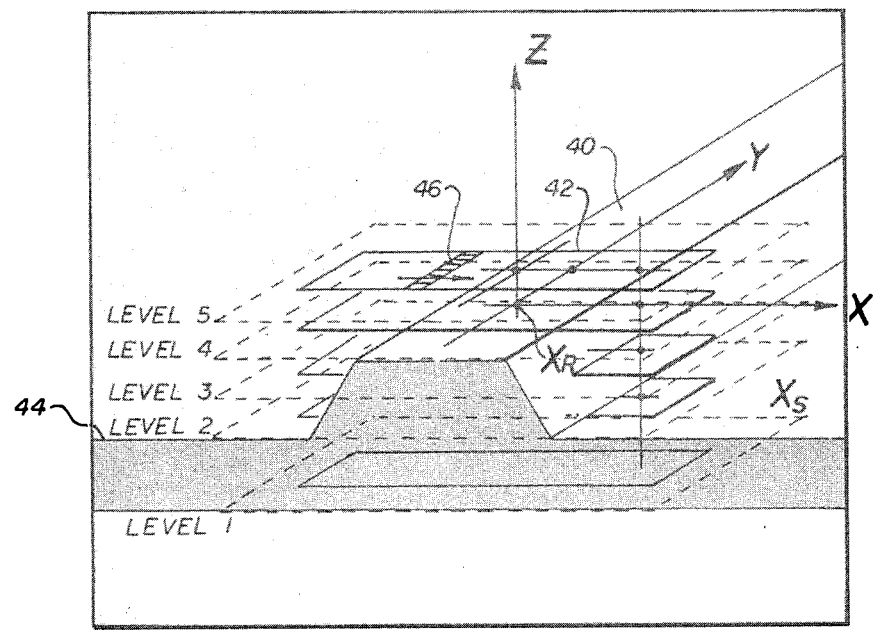
FIG. 2 is an isometric diagram illustrating an integrated circuit line and five inspection levels.
Figure 8:
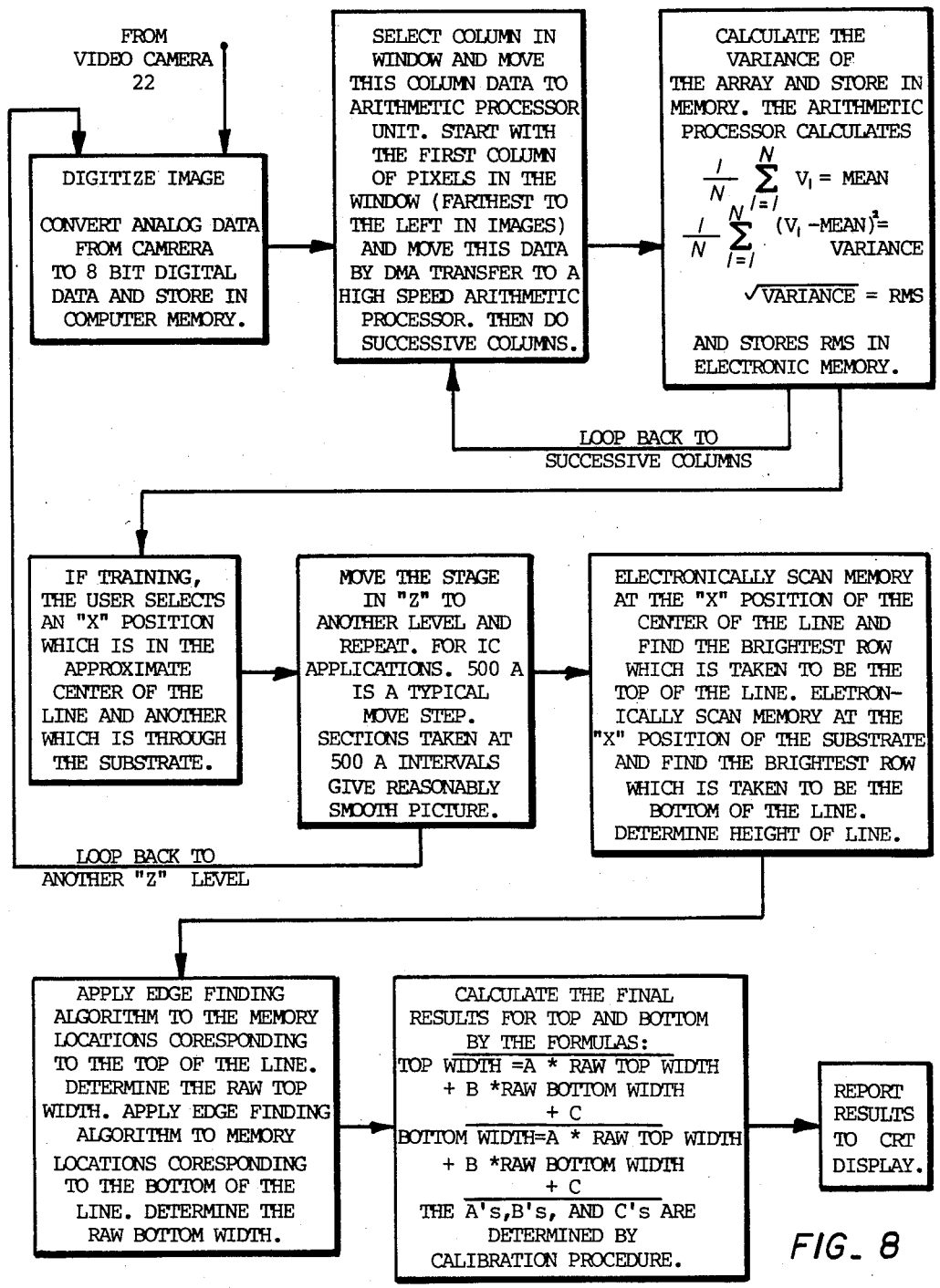
Figure 10:
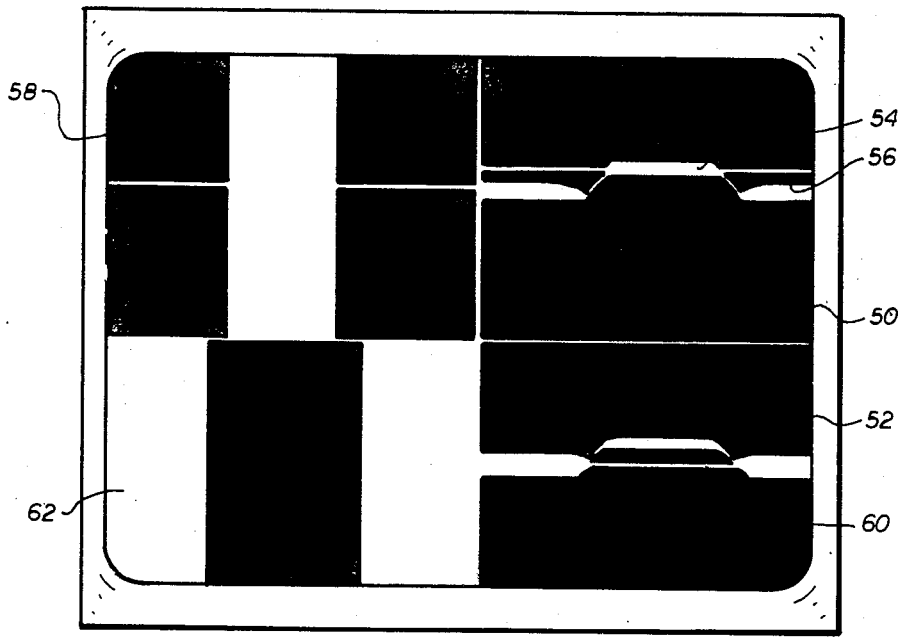
Figure 9:
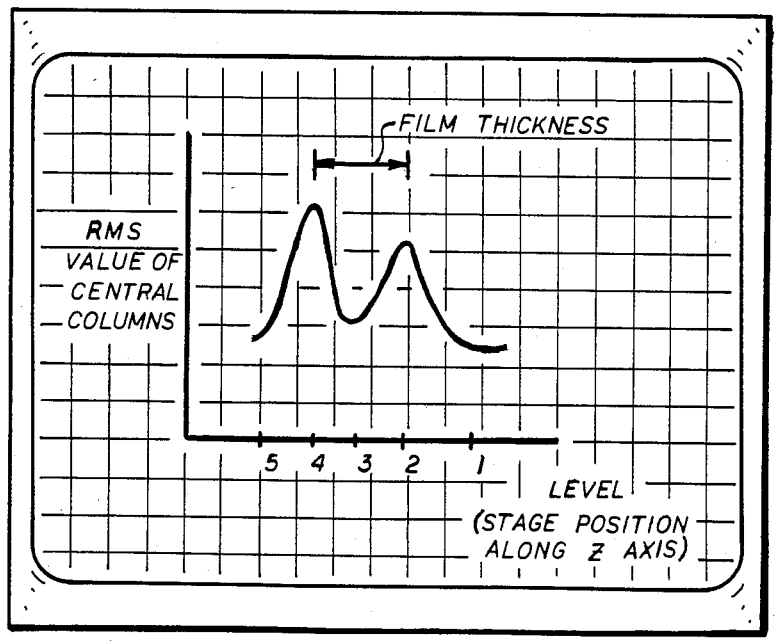

FIGS. 3 through 7 are actual photographic depictions of interference images taken at the levels 5 through 1 respectively, of FIG. 2;

FIG. 8 is a flow diagram functionally depicting operation of the electronic processing electronics of the present invention;

FIG. 9 is an RMS profile of a central column developed in accordance with the present invention; and FIG. 10 is a depiction of a CRT display in accordance with the present invention.

DETAILED DESCRIPTION OF THE PREFERRED EMBODIMENT

Interference microscopes can measure the topography of reflective surfaces using standard techniques so long as the undulations in relief are within the depth of field of the imaging system, and so long as the topography is not so jagged as to confuse the fringe counting algorithm. The basic formula is $$\Delta h = \frac{\Delta \phi}{2\pi} \frac{\lambda}{2} \tag{1}$$

where $\Delta h$ is the difference in height between two points in the image, $\Delta \phi$ is the phase difference, and $\lambda$ is the wave length of light. The standard applications of the Linnik microscope in this context are given in "Incident-Light Microscope Inteferometer for the Orthoplan and Metalloplan", *Instruction Manual for Use of the Linnik Microscope Attachment* by Ernst Leitz Gmbh, Wetzlar (1980); and in LEITZ, "Incident-Light Interference Illuminator for the Orthoplan/Metalloplan, a module which uses the wave length of light for measurement (19__)".

However, these standard techniques break down when any of the following three conditions are present:

1. The topographic fluctuations on the object surface within the field of view exceed the depth of focus of the microscope;
2. The object consists of transparent structures formed on an opaque substrate; or
3. The object surface has steep cliffs or walls the vertical extent of which exceeds a half wavelength of light.

When any of these cases occur, as they often do in integrated circuit devices, the standard use of the Linnik or other two beam interference microscopes simply does not give useful data because the fringe counting algorithm provides hopelessly confused and incorrect results when combined with equation 1.

The analysis process of the present invention described hereinafter overcomes the difficulties encountered by the standard techniques of Linnik interference microscopy, and when implemented in electronic hardware offers new capabilities for automated inspection of semiconductor devices.

The basic concept of the present invention is that broad band illumination (white light) has a very short coherence length, and by measuring the degree of coherence between an object and a reference beam at each point in an image, a powerful light sectioning technique may be developed.

The principle can be illustrated with scalar diffraction theory. However, the basic ideas apply in general even when scalar diffraction theory does not provide a good approximation.

Consider the wave equation of light in a homogeneous medium:

$$\left[ \frac{\partial^2}{\partial t^2} - c^2 \Delta \right] U(x,t) = 0 \quad (2)$$

where c is the speed of light in the medium and u may be written as a Fourier integral in the form $$U(x,t) = \int \frac{d^3K}{(2\pi)^3} e^{i(K \cdot x - \omega_K t)} U(K) \quad (3)$$

$$\omega_K = c \sqrt{K^2} \quad (4)$$

The spectral density is $$\rho(\omega) = \alpha \int \frac{d^3K}{(2\pi)^3} \delta(\omega - \omega_K) |U(K)|^2 \quad (5)$$

where $\alpha$ is a normalization constant and $\delta$ is a delta function. The degree of first order coherence is $$g(x_1,t_1;x_2,t_2) = \frac{|<U^*(x_1,t_1)U(x_2,t_2)>|}{(<|U(x_1,t_1)|^2><|U(x_2,t_2)|^2>)^{\frac{1}{2}}} \quad (6)$$

where the brackets $<>$ denote ensemble average. If the wave u is a sum of two constituent waves:

$$U = U_1 + U_2 \quad (7)$$

then the degree of coherence between $U_1$ and $U_2$ may be defined analogously as $$G(x,t) = \frac{|<U_1^*(x,t)U_2(x,t)>|}{(<|U_1(x,t)|^2><|U_2(x,t)|^2>)^{\frac{1}{2}}} \quad (8)$$

Figure 1:
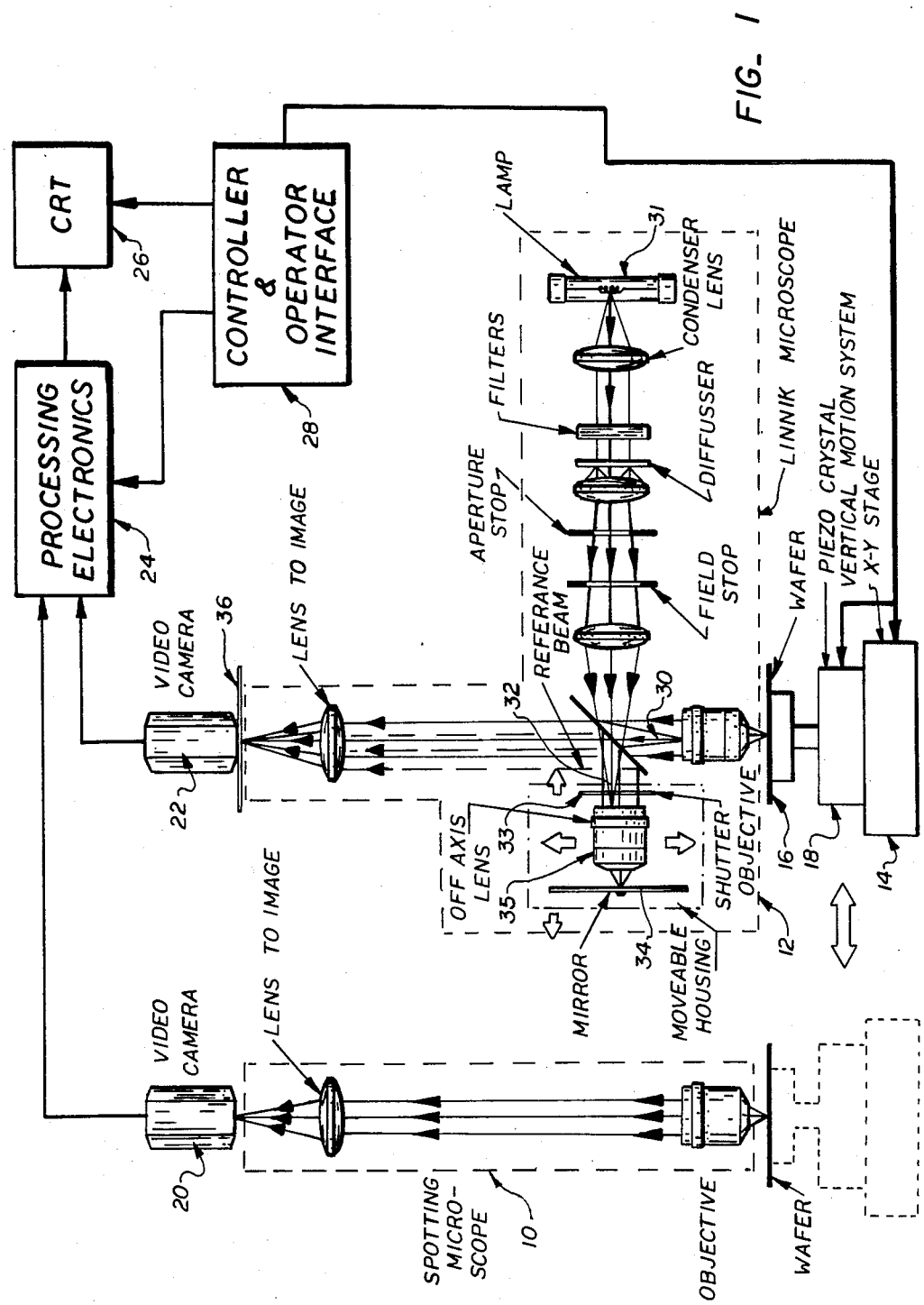
FIG. 1 is a schematic diagram depicting the basic functional components of the present invention.

Referring now to FIG. 1 of the drawing, apparatus in accordance with the present invention is schematically shown to include a spotting microscope 10, a LINNIK microscope 12, an X,Y stage 14 for carrying a wafer 16 and a piezo-electric vertical motion system 18 between a set up position beneath microscope 10 and an inspection position beneath microscope 12, a pair of video cameras 20 and 22, data processing electronics 24, a CRT display 26 and an electronic controller and operator interface console 28.

In a two-beam interference microscope (such as the Linnik microscope), a light wave from a source 31 reaching the image plane 36 is the sum of two constituent waves; one reflecting off the surface of the object 16, and the other reflecting off the surface of a reference mirror 34. Fringes are seen in the image at 36, even when white light is used to illuminate the object. If broad band illumination (white light) is used, strongest fringing occurs when the path difference between the reference channel 32 and the object channel 30 is very small, on the order of a fraction of the average wavelength, because the coherence length of white light is very short. When the degree of coherence is high between the reference channel and the object channel, the fringes are strong. Conversely, when the degree of coherence is low, the fringes are weak. In the preferred embodiment, white light Kohler illumination is provided by a Xenon arc lamp 31, and a shutter 33 is included to flip the reference beam in and out. The fringe rate and direction can be controlled on commercially available Linnik microscopes by moving the microscope objective in the reference channel off-axis. Accordingly, in the preferred embodiment the lens 35 is positioned to make the fringes which appear at image plane 36 be parallel to camera 22's raster direction and the fringe spacing equal to 32 horizontal raster rows of camera 22.

The connection between degree of coherence and fringe intensity may be described as follows where $U_1$ is the object wave and $U_2$ is the reference wave. At the image plane, the superposition of the object and the reference wave results in the light intensity $$<|U_1+U_2|^2> = <|U_1|^2> + <|U_2|^2> + 2R_e<U_1^*U_2> \quad (9)$$

The overall path length difference between the reference channel and the object channel can be varied so as to introduce a phase difference between the object channel and the reference channel. In the narrow bandwidth approximation, the phase shift will be the same for all frequencies of the light. In this case, intensities at the image plane are of the form $$<|U_1+e^{i\phi}U_2|^2> = <|U_1|^2> + <|U_2|^2> + 2R_e[e^{i\phi}<U_1^*U_2>] \quad (10)$$

The variance in equation 10, calculated by letting $\phi$ vary from $-\pi$ to $\pi$ is easily found to be $$\text{Variance of } <|U_1+U_2e^{i\phi}|^2> = 2|<U_i^*U_2>|^2 \quad (11)$$

and therefore the degree of coherence may be expressed as $$G = \frac{\sqrt{\frac{1}{2} \text{Variance of} <|U_1 + e^{i\phi}U_2|^2>}}{(<|U_1|^2><|U_2|^2>)^{\frac{1}{2}}} \quad (12)$$

In the present case, the illumination is actually broad band and the phase shift is different for the different frequencies of the light. However, in this case it is found that the following functional form for $<U_1^*U_2>$ is a good approximation for images taken in a two beam interference microscope:

$$<U_1^*U_2> = me^{R(l)}e^{ilK(l)}, \quad l=\text{path difference,} \quad (13)$$

where $R(l)$ and $K(l)$ are slowly varying over the distance $2\pi/K(l)$ and therefore equation (12) is still derivable provided that is made to vary through $2\pi$ by letting l vary from $-\pi/K(l)$ to $\pi/K(l)$ in the calculation of the variance. The parameter "m" in equation (13) is a complex constant.

Therefore, one can define an easily measurable quantity $C(x,t)$ which may be taken as a practical measure of the degree of coherence as $$C(x,t) = \sqrt{\frac{1}{2} \text{Variance over path } l \text{ of } <|U_1 + U_2|^2>} \quad (14)$$

If $U_1$ and $U_2$ are not coherent, then C=0. In general, assuming that $R(l)$ and $K(l)$ are slowly varying in equation (13), it can be shown that $$C = (<|U_1|^2><|U_2|^2>)^{\frac{1}{2}}G \quad (15)$$

The technique of the present invention is to synthetically construct images the brightness of which at each image point is proportional to C. This amounts to imaging by means of a coherence probe.

The interference microscope 12 is set up in the following way prior to calculation of C: With a first surface mirror (not shown) as the object (at 16), the focus in the object channel 30 and the reference channel 32 are adjusted so that both the reference mirror 34 and the object mirror are simultaneously in focus. Then the path difference is adjusted until the maximum degree of coherence is obtained between the object wave and the reference wave. This reference position is then the center point in the variation of path difference used to measure the degree of coherence.

If fringe data is being used, as described below the setup is a little different. In such case, a window in the center of the image plane 36 is selected as the area of interest, and after focusing the reference and object mirrors, the path is adjusted so that the fringe amplitude is the greatest at center of the window. The object mirror is then replaced by an object such as a silicon wafer 16 having an integrated circuit formed in its upper surface.

All parts of the object surface which are at the same "level" as the surface of the reference mirror will now produce a scattered wave which is relatively coherent with respect to the reference wave, and those image points end up being bright in the final image at 36 (FIG. 1). The very brightest points are those where the object locally is a horizontally reflective surface because at those points the object wave and reference wave match is best. Parts of the object which are at a different level than the reference mirror appear dark. Sectioning can then be accomplished by moving the wafer 16 up or down to obtain successive images corresponding to respective object planes passing through the wafer 16, as illustrated in FIG. 2.

The degree of coherence C can be measured in a Linnik microscope in several ways. One way is to vary the path length of the reference channel 32; for example, through one or more wavelengths centered on the reference position, and while doing this, calculating electronically the oscillation in intensity at each point in the image plane of the microscope. The amplitude of oscillation (variance) is proportional to C.

Alternatively, for object surface features which do not vary too quickly in one direction (such as in the case of a semiconductor integrated circuit line) the interference fringes may be adjusted so that they lie perpendicular to a line to be inspected. The fringe spacing may also be adjusted to any convenient value. In this case C is simply the amplitude of the fringes within the window, i.e., $$C = \text{Fringe Amplitude} \quad (16)$$

The advantage of this technique is that, as will be further explained below, only one image is required to make a measurement of C at all points across the line.

FIGS. 3–7 show photographs of actual fringe data taken at the different object elevations generally depicted in FIG. 2. The object in this case was a silicon wafer having a one micron high resist line 40 formed on its upper surface. The vertical and horizontal white lines depicted in the photographs are an electronic overlay produced on the display CRT 26 and can be ignored for this discussion. The resist portion 40 is in the center of each photo, and as depicted in FIG. 2, the five photos of FIGS. 3–7 are taken at different positions of the object along the vertical (or Z) axis.

Figure 3:
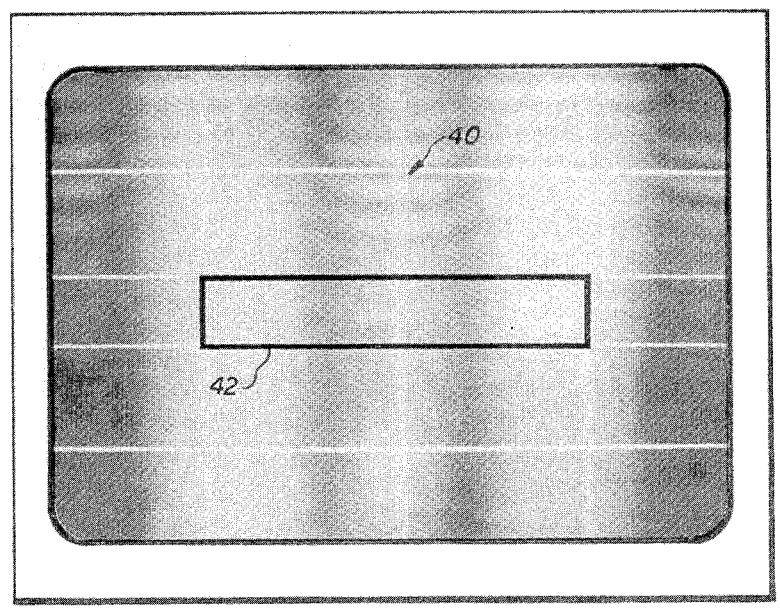
Figure 6:
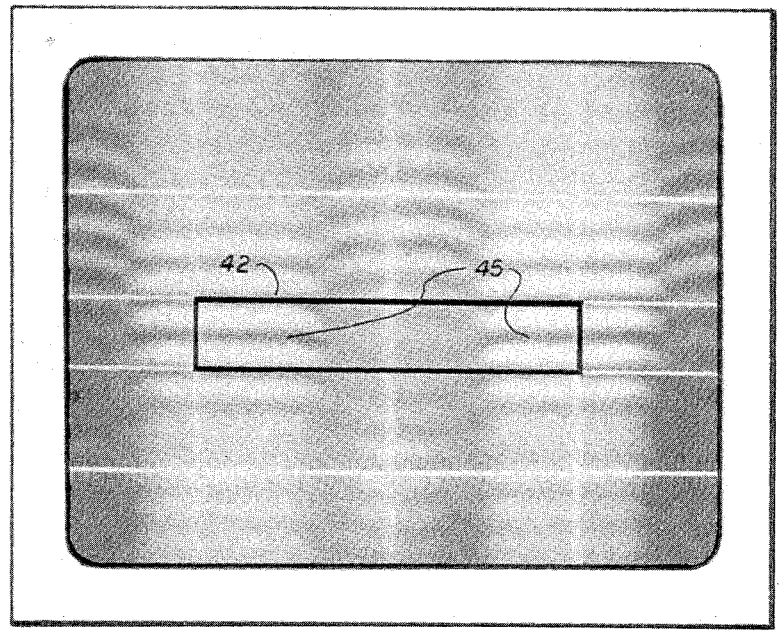

More specifically, the plane of focus of the image shown in FIG. 3 is slightly above the top surface of the resist line 40, i.e., at level 5 in FIG. 2. Within the central window 42, framed in black in the photos, the fringe intensity is shown to be weak.

FIG. 4 shows the wafer raised a few thousand Angstroms to bring the top of the resist into focus (at level 4 of FIG. 2). Fringes 43 in the window 42 are now strong in the central portion of the image (corresponding to the top surface of the resist) but are weak on either side (where no resist is present).

FIG. 5 shows the wafer again raised an additional few thousand Angstroms so that the focal plane is between the top level of the resist and the silicon substrate (level 3 in FIG. 2). Here again, the fringes are weak in both the resist region and the silicon region since neither is in focus.

In FIG. 6 the wafer has again been raised another few thousand Angstroms to level 2 to bring the silicon surface 44 (FIG. 2) into focus. Here the fringes 45 are strong on the silicon and are fairly weak in the resist portion of the image.

Figure 7:
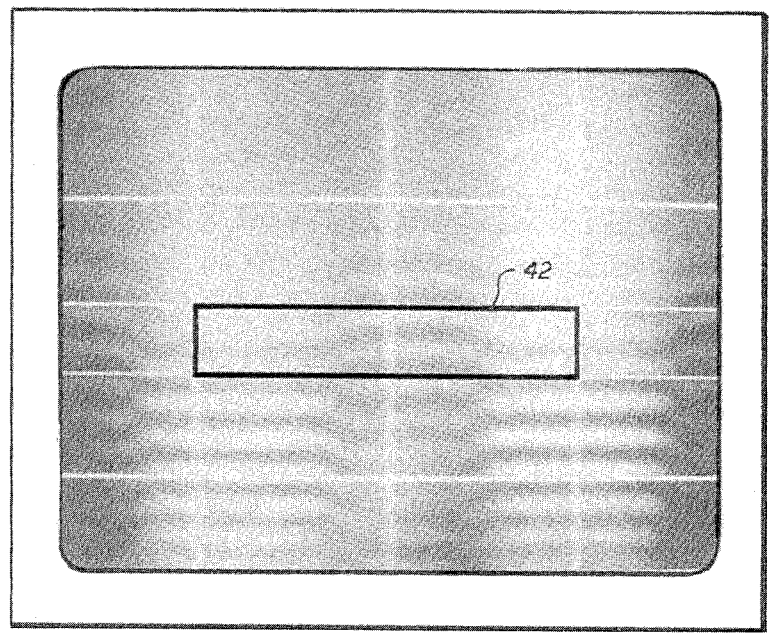

In FIG. 7, only the resist shows strong fringing due to the reflection of the light off the bottom of the resist layer.

The process by which fringe amplitudes are used to measure line widths on integrated circuits is shown in the flow chart of FIG. 8. The boxes describe the algorithms used. The "column in window" reference in FIG. 8 refers to the columns of pixels, one of which is shown at 46 in FIG. 2, scanned by the processor 24 to determine the variance values over the length of the window 42, to thereby calculate the fringe coherence.

More particularly, the image 36 is scanned by video camera 22, which develops an analog raster scan thereof for input to the processing electronics 24. The first processing step is to convert the analog data into 8 bit digital form and to store the data in a computer memory. A "window" such as is illustrated at 42 in FIG. 2, is then scanned a pixel column at a time, as illustrated at 46 and the data corresponding to each column is moved by DMA transfer to a high speed arithmetic processor which calculates the variance of each columnar array and stores its RMS value in memory. After data is collected across the window 42 the stage is incremented in the Z direction to another level, another scanning operation is completed and the data stored. This operation is repeated at levels separated by approximately 500 Angstroms until sufficient data is obtained to evaluate all desired surfaces. The several sets of scan data stored in memory is then itself scanned at the centermost point $X_R$ in "X" of the resist line 40 (along the Z axis in FIG. 2) to determine the level having the highest RMS value, and such level is determined to coincide with and thus identify the top of the scanned line.

One such electronic scan is depicted in FIG. 9 wherein the ordinate represents the RMS value of the central column data and the abscissa represents the inspection level (or stage position along the Z axis). As illustrated, the peak at level 4 corresponds to the top of the resist line 40 of FIG. 2 while the peak at level 2 corresponds to reflection off the wafer substrate 44. The horizontal distance between the two peaks is thus an indication of the vertical thickness of the resist line 40.

The memory is thereafter scanned at an X position $X_s$ over only the substrate to find the scan line having the brightest level and this is taken to be the bottom of the line. By subtracting the top level from this bottom level information the height of the line can be determined.

The next step is to apply an edge finding algorithm to the memory location corresponding to the top of the line in order to determine the raw top width. An edge finding algorithm is then applied to the memory location corresponding to the bottom of the line to determine the raw bottom width. The final results for top and bottom width are calculated from the formulas top width=$A_1$* raw top width+$B_1$* raw bottom width+$C_1$ bottom width=$A_2$* raw top width+$B_2$* raw bottom width+$C_2$.

The constants A, B, and C are determined by calibration procedure. Once these widths are determined they can be reported to the CRT and displayed to the user.

FIG. 10 shows an artist's rendition of the synthetic images produced on a CRT screen by imaging C. The upper and lower righthand quadrants 50 and 52 show cross sections of the line, each row corresponding to a different level (scan line). The elevated resist 54 appears as a cloud above the silicon substrate. An electronic line 56 has been drawn in the right upper quadrant through the algorithm's choice as the best row to call the top of the line.

The upper left hand quadrant 58 shows this row expanded vertically to fill the entire quadrant and to thereby look like a top down view. The lower right hand quadrant 52 showns a line 60 drawn through the algorithm's choice as the best candidate for the bottom substrate level.

The lower left quadrant 62 depicts an expanded top down view of the line 60. The edge finding algorithm then uses a threshold technique to find the edges in both the upper and lower left hand quadrants.

In this way the height is known (by the difference in stage position between the top and bottom rows), the top width is known by the distance between the edges in the upper left quadrant, the bottom width is known by the distance between the edges in the bottom left quadrant, and the wall angles may be calculated. For best results, calibration to scanning electron microscope results are required.

In operation the technique consists of first aligning a semiconductor IC line (such as 40 in FIG. 2) in the field of view of the spotting microscope 10. The wafer is then moved a fixed offset to the right, as illustrated in FIG. 1, so that the same line is now viewed by the Linnik microscope 12. The interference fringes are then preadjusted to lie perpendicular to the line direction, and the fringe spacing is adjusted to have two complete fringes within the window (of variance calculation) 42 (FIGS. 3-7) when a reflective plane in the object is in focus (see FIG. 4 for example.

The wafer is then dropped in the z direction so that the highest point in the line is several thousand Angstroms below the focal plane, and the resulting image at 36 is digitized by the electronics 24. The fringe amplitude is then calculated for each scan column 46 (FIG. 2) in the window 42, and the result is stored in memory.

One method of calculating the fringe coherence is to calculate the variance of each column array 46 (FIG. 2) across the window 42. To accomplish this for each array 46, the arithmetic processor in the electronics 24 calculates:

$$\text{Mean} = \frac{1}{N} \sum_{i=1}^{N} V_i$$

$$\text{Variance} = \frac{1}{N} \sum_{i=1}^{N} (V_i - \text{Mean})^2$$

$$RMS = \sqrt{\text{Variance}}$$

The stage is then moved up a small distance (about 500 Angstroms) and another image is digitized, fringe amplitudes calculated, and results stored. The process of moving the stage up, digitizing the image, and storing the fringe amplitudes is repeated until the stage has scanned a sufficient distance to place the lowest point of the line above the optics focal plane so that the entire depth of the line has been sectioned.

The top and bottom levels of the line are then determined by finding the brightest scan rows at the appropriate positions in the image. Then the edges of the line at the top and bottom levels are determined by an edge finding algorithm. Finally, the output data is calculated by means of a calibration formula which calculates the top and bottom width by the formulas:

Top width=$A_1$*(Raw top width)+$B_1$*(Raw bottom width )+$C_1$

Bottom width=$A_2$*(Raw top width)+$B_2$*(Raw bottom width)+$C_2$ where $A_1$, $A_2$, $B_1$, $B_2$, $C_1$ and $C_2$ are determined by a calibration procedure, and the results maybe reported to the CRT 26. The results consist of the top width and bottom width, as well as the positions of the four edges used in the calculation of the vertical wall angles.

Although the present invention has been illustrated in a preferred embodiment, it is anticipated that following a reading of this disclosure numerous alterations and modifications thereof will become apparent to those skilled in the art. It is therefore intended that the appended claims be interpretted as covering all such embodiments as fall within the true spirit and scope of the invention.

What is claimed is:

1. A method of inspecting an object and generating synthetic image data comprising the steps of:
   (a) using an interference optical system including an object channel and a reference channel for simultaneously inspecting an object and a reflective reference surface and developing a plurality of images formed by the interference between object wave energy passing from said object and through said object channel to an image plane and reference wave energy passing from said reference surface and through said reference channel to said image plane, each said image being formed in response to a change in position of either said object or said reference surface;
   (b) determining for each image the absolute value of the degree of coherence between said object wave energy and said reference wave energy by calculating the variance along each column of an array of m×n pixels in said image plane, where m and n are integers, and generating absolute value coherence data corresponding to each said column; and
   (c) using said absolute value coherence data to generate synthetic image data representative of a particular characteristic of said object, wherein the brightness of each pixel element of a synthetic image developed using said synthetic image data is proportional to said absolute value coherence data.

2. A process for generating synthetic image data representative of a cross-section of an at least partially reflective irregular surface of an object formed by a portion of a semiconductor wafer having an elongated strip of raised surface extending therethrough, comprising the steps of:
   (a) illuminating the irregular object surface with light from a source of illumination;
   (b) illuminating a reflective reference surface with light from said source of illumination, said reference surface being formed by an optically flat mirror;
   (c) collecting object light reflected from said object surface and directing said object light along a first optical axis;
   (d) collecting reference light reflected from said reference surface and directing said reference light along a second optical axis at least a portion of which is parallel to said first optical axis;
   (e) focussing the light directed along said first and second optical axes to form a fringed image pattern resulting from interference of said object light and said reference light;
   (f) orientating said wafer so that a selected scan line may be directed substantially orthogonal relative to the length of said elongated strip;
   (g) inspecting said image pattern to develop a series of coherence data corresponding to the fringe amplitude at points along said scan line;
   (h) incrementally changing the position of said object along said first optical axis, each time repeating steps (a) through (e) and (g);
   (i) processing the plurality of series of coherence data to develop synthetic image data corresponding to a cross-sectional profile of said object surface taken in a plane including said selected scan lines;
   (j) displaying said synthetic image data to visually depict a cross-sectional profile of said object surface taken in the plane including said scan lines; and
   (k) determining the position of said object along said first optical axis at which the value of said coherence data corresponding to the crossing of a first particular scan line over said raised surface is at a maximum relative to the corresponding coherence data of the other scan lines and identifying this position as corresponding to the top surface of said strip.

3. A process as recited in claim 2, and further comprising the step of;
   (l) detecting the width of the top of said raised surface by measuring the length of the portion of said first particular scan line over which said coherence data is at a maximum.

4. A process as recited in claim 3, and further comprising the steps of;
   (m) determining the position of said object along said first optical axis when the value of said coherence data corresponding to the crossing of another particular scan line over portions of said surface other than said raised surface are at a maximum relative to the corresponding data of the other scanned lines; and
   (n) determining the width of the base of said raised surface by measuring the separation between the portions of said other particular scan lines over which said data is at a maximum.

5. A process as recited in claim 4, and further comprising the step of:
   (o) determining the height of said raised surface above the adjacent wafer surface by measuring the distance between the position at which the object is positioned along said first optical axis when the width of the top of said raised surface is detected and the position along said first optical axis when the width of the base of said raised surface is detected.

6. A process as recited in claim 5 and further comprising the step of;
   (p) calculating the slopes of the side walls of said raised surface, in the plane including said scan lines, as a function of the height of the top of the raised surface above the base thereof and the difference in width of the top and the base along the corresponding scan lines.

7. A process as recited in claim 2, wherein said synthetic image data is developed by calculating the intensity of the interference fringes in said fringed image pattern and by calculating the local variance of the image intensity caused by the fringes.

8. A process as recited in claim 2, wherein said synthetic image data is generated by calculating the variance of the intensity of each pixel in the image plane as the path difference between the first and second optical paths is made to change.

9. A method of measuring certain dimensions of an elongated strip of raised surface formed on an object, such as a semiconductor wafer or photomask, using an interference optical system to develop images formed by interference between object wave energy passing from the object and through an object channel to an image plane and reference wave energy passing through a reference channel to the image plane, comprising the steps of:

(a) illuminating the object surface with light from a source of illumination;

(b) illuminating a reflective reference surface with light from said source of illumination;

(c) collecting object light reflected from said object surface and directed along a first optical axis through said object channel;

(d) collecting reference light reflected from said reference surface and directed along a second optical axis through said reference channel, said second optical axis having at least a portion thereof which is parallel to said first optical axis;

(e) focusing the light directed along said parallel portions of said first and second optical axes onto an image plane to form an interference image pattern resulting from interference of said object light and said reference light;

(f) inspecting the image pattern by detecting the light intensity at each pixel in an array of mxn pixels extending across the image of said strip to produce pixel data;

(g) scanning the pixel data and calculating therefrom coherence data representing the absolute value or magnitude of the complex degree of coherence of light incident upon said image plane and storing the calculated coherence data for subsequent reference;

(h) incrementally changing the position of said object along said first optical axis, each time repeating steps (a) through (g); and (i) using the stored coherence data to generate data from which a synthetic image corresponding to a transverse cross-section of the measured strip may be developed.

10. A method as recited in claim 9 and further including the step of:

inspecting the stored coherence data to determine the height of the top surface of said strip relative to the adjacent surface of said object, such height being measured by determining a first position along said first optical axis at which maximum coherence occurs at a point in an array corresponding with said top surface, and by determining a second position along said first optical axis at which maximum coherence occurs at a point in an array corresponding with said adjacent surface, the measured height of said top surface being equal to the distance between said first position and said second position.

11. A method as recited in claim 10 and further comprising the step of determining the width of the top surface of said strip by applying an edge finding algorithm to coherence data taken from the image corresponding to said top surface.

12. A method as recited in claim 10 and further comprising the step of measuring the width of the bottom of the strip by applying an edge finding algorithm to coherence data taken from the image corresponding to said adjacent surface.

13. A method as recited in claim 9 wherein the step of calculating the absolute value or magnitude of the complex degree of coherence is accomplished by measuring the variance of the interference image along pixel columns of an mxn array inspected at each position of said object along said optical axis.

14. A method as recited in claim 9 wherein the step of calculating the absolute value or magnitude of the complex degree of coherence is accomplished by calculating the variance of the light intensity among corresponding pixels of the several image patterns inspected as the position of said object is changed along said first optical axis producing a change in the path difference between said object channel and said reference channel.

15. A method as recited in claim 9 wherein the step of calculating the absolute value or magnitude of the complex degree of coherence is accomplished by calculating the variance of the light intensity among corresponding pixels of the several image patterns inspected as the position of said reference mirror is changed along said second optical axis producing a change in the path difference between said object channel and said reference channel.

16. A method of inspecting an object and generating synthetic image data comprising the steps of:

(a) using an interference optical system including an object channel and a reference channel for simultaneously inspecting an object and a reflective reference surface and developing a plurality of images formed by the interference between object wave energy passing from said object and through said object channel to an image plane and reference wave energy passing from said reference surface and through said reference channel to said image plane, each said image being formed in response to a change in position of either said object or said reference surface (b) determining for each image the absolute value of the degree of coherence between said object wave energy and said reference wave energy by calculating the variance in the intensity of each pixel over the said plurality of images and generating corresponding absolute value coherence data; and (c) using said absolute value coherence data to generate synthetic image data representative of a particular characteristic of said object, wherein the brightness of each pixel element of a synthetic image developed using said synthetic image data is proportional to said absolute value coherence data.

* * * * *